(12) United States Patent
Hjelme et al.

(10) Patent No.: US 7,616,844 B2
(45) Date of Patent: Nov. 10, 2009

(54) FABRICATION OF FIBER OPTIC PROBES

(75) Inventors: Dag Roar Hjelme, Trondheim (NO); Oddvar Aune, Trondheim (NO); Berit Falch, Trondheim (NO); Dan Ostling, Trondheim (NO); Reinold Ellingsen, Trondheim (NO)

(73) Assignee: InvivoSense AS, Trondheim (NO)

( * ) Notice: Subject to any disclaimer, the term of this patent is extended or adjusted under 35 U.S.C. 154(b) by 0 days.

(21) Appl. No.: 12/282,694

(22) PCT Filed: Mar. 14, 2007

(86) PCT No.: PCT/GB2007/000881

§ 371 (c)(1),
(2), (4) Date: Nov. 26, 2008

(87) PCT Pub. No.: WO2007/104974

PCT Pub. Date: Sep. 20, 2007

(65) Prior Publication Data

US 2009/0074349 A1 Mar. 19, 2009

(30) Foreign Application Priority Data

Mar. 14, 2006 (GB) ................... 0605108.0

(51) Int. Cl.
*G02B 6/00* (2006.01)
(52) U.S. Cl. .......................... 385/12; 385/13
(58) Field of Classification Search .............. 385/12, 385/13, 115–118, 149
See application file for complete search history.

(56) References Cited

U.S. PATENT DOCUMENTS

| 4,842,783 A | 6/1989 | Blaylock |
| 5,132,057 A | 7/1992 | Tomisaka et al. |
| 5,611,998 A | 3/1997 | Aussenegg et al. |
| 5,898,004 A | 4/1999 | Asher et al. |
| 5,919,712 A * | 7/1999 | Herron et al. ............... 436/518 |
| 7,470,549 B2 * | 12/2008 | Yamamoto et al. .......... 436/518 |
| 2003/0053050 A1 | 3/2003 | Potyrailo et al. |
| 2003/0171666 A1 | 9/2003 | Loeb et al. |

FOREIGN PATENT DOCUMENTS

| JP | 2002-187139 A1 | 7/2002 |
| WO | 03034047 A1 | 4/2003 |

OTHER PUBLICATIONS

International Search Report for PCT/GB2007/000881 dated May 9, 2007.

(Continued)

*Primary Examiner*—Kevin S Wood
(74) *Attorney, Agent, or Firm*—McCormick, Paulding & Huber LLP

(57) ABSTRACT

A method of fabricating a sensor probe comprises:
placing the end of an optical fiber 10 in a polymerization space 2;
applying a drop of hydrogel pre-gel solution 30 to the end of the fiber;
exposing said pre-gel solution to an ultra-violet light source 24 to cause polymerization therein; and
monitoring a light signal that has passed down said optical fiber 10 in order to monitor said polymerization.

49 Claims, 5 Drawing Sheets

OTHER PUBLICATIONS

Cusano, A., et al., "An Integrated Fiber Optic Sensing System for in Situ Characterization of the Curing Process of Thermoset Based Composites", Proceedings of the SPIE—The International Society for Optical Engineering SPIE-Int., Soc. Opt., ENG. USA, vol. 4328, pp. 275-284 (2001).

Santos, A.F. et al., "Monitoring and Control of Polymerization Reactors Using NIR Spectroscopy", Polylmer-Plastics Technology and Engineering, Marcel Dekker USA, vol. 44, No. 1, pp. 1-61 (2005).

Seitz, W.R., et al., "Derivatized, Swellable Polymer Microspheres for Chemical Transduction", Analytica Chimica Acta, vol. 400, pp. 55-64 (1999).

* cited by examiner

US 7,616,844 B2

FABRICATION OF FIBER OPTIC PROBES

CROSS REFERENCE TO RELATED APPLICATIONS

This application is entitled to the benefit of and incorporates by reference essential subject matter disclosed in International Patent Application No. PCT/GB2007/000881 filed on Mar. 14, 2007 and Great Britain Patent Application No. 0605108.0 filed Mar. 14, 2006.

TECHNICAL FIELD

This invention relates to the fabrication of interferometric fibre optic probes employing hydrogel sensor material that is responsive to an analyte; and to probes produced thereby. It relates particularly, but not exclusively, to probes which are suitable for invasive measurements of analytes in a live body.

BACKGROUND OF THE INVENTION

When a hydrogel is placed in a solvent it absorbs solvent until it reaches an equilibrium swelling when the reactive forces balance the swelling forces. Any binding process that modifies the affinity of the polymer chains to the solvent will change the equilibrium swelling. Alternatively, any interaction that modifies the degree of cross-linking in the polymer network will also change the equilibrium swelling. The binding processes may also modify the refractive index of the hydrogel, either through a changed volume fraction of polymer or through the presence of additional molecules bound to the polymer chains.

This change in volume and/or refractive index which such hydrogels exhibit when a particular analyte is present can be measured to determine the concentration of that analyte in the solvent. Various methods can be used to measure these changes in the hydrogel but optical measurement and particularly interferometric measurement is an especially attractive technique since it allows dimensional changes to be accurately measured. The hydrogel forms a Fabry-Perot optical cavity from which an interference signal is produced.

Various optical sensor devices using hydrogel swelling have been proposed. For example, U.S. Pat. No. 5,898,004 (Polymerized Crystalline Colloidal Array Sensor, Asher et. al.) disclose a device composed of crystalline colloidal array polymerized in a hydrogel. The hydrogel swelling is measured as a shift in the Bragg diffraction wavelength. U.S. Pat. No. 5,611,998 (Optochemical Sensor And Method For Presentation, Aussenegg at. al.) discloses a sensor composed of small metallic islands on top of a thin layer of swellable polymer backed by a mirror. The film structure is characterized by strong narrow reflection minima whose spectral position is sensitive to the polymer thickness. Various sensor devices are also reported in the art. For example, Seitz et. al. ("Derivatized, swellable polymer microspheres for chemical transduction," Analytica Chimica Acta, vol. 400, pp 55-64, 1999) disclose a device composed of swellable polymer microspheres incorporated in a hydrogel. Turbidity spectra are affected by the microsphere swelling.

Various fiber optical chemical and physical sensor devices using thin polymer layers at the optical fiber end face have also been reported. These prior approaches have many limitations. Sensors based on polymer films, or drops, are too dense to allow macromolecules to diffuse in to the sensor material. Furthermore, sensors based on fluorescence, scattering or intensity modulation are made to avoid specular reflection from the polymer surface since specular reflection will interfere with the sensor signal. On the other hand previously proposed interferometric sensors all use polymer sensor material in the form of thin planar layer or disk on the fiber end. The inventors have appreciated that these have a less than optimal optical coupling to the fiber waveguide mode; and a less than optimal speed of diffusion response. It is an object of the invention to improve these characteristics.

Our earlier PCT application published under number WO03/034047 discloses various arrangements for the interferometric measurement of swelling and/or refractive index changes of a hydrogel mass at the end of an optical fiber. Also disclosed in that application is a technique for making such fiber sensors which comprises covering a pre-gel material with a lid before gelation.

BRIEF SUMMARY OF THE INVENTION

It is an object of the invention to improve the fabrication of sensors. When viewed from a first aspect the invention provides a method of fabricating a sensor probe comprising:
  a. placing the end of an optical fiber in a polymerization space;
  b. applying a drop of hydrogel pre-gel solution to the end of the fiber;
  c. exposing said pre-gel solution to an ultra-violet light source to cause polymerization therein; and
  d. monitoring a light signal that has passed down said optical fiber in order to monitor said polymerization.

When viewed from a second aspect the invention provides apparatus for fabricating a sensor probe comprising:
  a. an optical fiber having a drop of hydrogel pre-gel solution on one end thereof;
  b. a polymerization space receiving said fiber end;
  c. an ultra-violet light source coupled to means for exposing said pre-gel solution to said light to cause polymerization therein; and
  d. means for monitoring a light signal that has passed down said optical fiber in order to monitor said polymerization.

The invention also extends to sensor probes made according to the method of the invention.

In accordance with the invention a high quality dome-shaped hydrogel sensor can be produced on the end of an optical fiber which allows interferometric measuring of changes in the sensor in response to target analytes. The Applicant has appreciated that the advantage of a dome-shaped sensor is that it maximises the speed of diffusion response for a given volume of hydrogel. It also enhances the optical coupling to the optical fiber wave guide mode by matching the optical phase fronts.

Furthermore in accordance with the invention polymerization of the hydrogel can be monitored by passing a light signal down the fiber which will form part of the sensor probe itself and measuring the resultant signal. This allows the quality of the sensor to be checked, in particular the homogeneity and the surface quality thereof.

There are many possible parameters and combinations of parameters relating to the polymerization process which can be monitored. Preferably the method of the invention comprises monitoring one or more parameters of the measured interference signal (normally a sinusoidal interferogram) from the group comprising: the average level of the signal, the variation of amplitude with wavelength, the period of the signal and the phase of the signal. The Applicant has found that the information about the quality of the droplet surface, its refractive index and scattering properties can be deduced from the average level and the variation of the amplitude with wavelength. The period of the variations and their phase allow the axial length and its rate of change respectively to be deduced.

The monitoring of the polymerization process may be passive in the sense that it may be used simply to ensure that a minimum threshold of quality is met. More preferably however it is used for active control of one or more parameters controlling the polymerization process. This could be by providing information to a user controlling the processing manually but preferably automatic feedback control is provided.

The Applicant has appreciated that in accordance with the invention monitoring of the polymerization process yields high quality dome-shaped hydrogel sensor probes. Furthermore however it has appreciated that by recording the polymerization process parameters that are employed to achieve such superior quality sensors, arrived at through the described monitoring, these parameters can be employed subsequently to produce further probes without the need to repeat the monitoring. Preferably therefore the method of the invention comprises storing one or more of the polymerization process parameters and using said parameter(s) to control a subsequent production of a sensor probe without monitoring. In other words the stored parameters may be used in a method comprising: placing the end of a further optical fiber in a polymerization space; applying a drop of said hydrogel pre-gel solution to the end of the further fiber, and exposing said pre-gel solution to an ultra-violet light source to cause polymerization.

Thus when viewed from a further aspect the invention provides a method of fabricating a plurality of sensor probes comprising:

a. placing the end of an optical fiber in a polymerization space;

b. applying a drop of hydrogel pre-gel solution to the end of the fiber; and c. exposing said pre-gel solution to an ultra-violet light source to cause polymerization therein wherein at least one of the temperature of the polymerization space, the exposure time of the ultra-violet light, the intensity of the ultra-violet light or the flux of the ultra-violet light is controlled according to a criterion predetermined from monitoring of a light signal that passed down an optical fiber during a previous production of a sensor probe in accordance with the invention.

In one set of embodiments the polymerization of the hydrogel takes place in a suitably inert gas. Preferably a continuous gas flow is maintained over the end of the fiber. The gas is preferably substantially free of oxygen since oxygen is a free radical scavenger which would be likely, if present, to quench the polymerization process. Preferably said gas comprises humidified nitrogen. Preferably the flow velocity and/or humidity of the gas is controlled in order to control evaporation of solvent from the pre-gel solution. Such control may be effected directly in response to the signal measured from the fiber where monitoring is used or in response to flow velocity and/or humidity sensors which can be used to maintain prior established values of these parameters.

More generally preferably one or more parameters of the polymerization process are controlled. Preferably said parameter(s) is/are selected from the group comprising: UV exposure time, intensity or flux; humidity; gas flow; and temperature. Preferably said parameter(s) is/are controlled to counter the heat generated by the polymerization reaction. Preferably at least one of temperature, humidity and gas velocity is controlled.

Preferably the partial pressure of water in the polymerization space is maintained at or near saturation pressure. This allows the volume of the gel droplet to be maintained either constant or, in some embodiments, slowly varying to optimise surface quality.

In some preferred embodiments the temperature of the polymerization space is controlled in order to match the heat generated by the polymerization reaction. This heat generation is a function of the monomer concentration, photo-initiator concentration and UV photon energy and flux. One or more parameters such as temperature may also be controlled in response to the absorption of UV light in the humid atmosphere.

In an alternative set of preferred embodiments the polymerization of the hydrogel takes place in a liquid. The liquid must be immiscible with the pre-gel solution in order that a clearly defined interface therewith is formed. The use of a liquid medium has several advantages. Firstly it has been found that the immiscible liquid interface referred to above makes the droplet on the end of the fiber more stable and thus easier to control. Secondly a liquid has a higher thermal conductivity and higher heat capacity than a gas thus allowing the heat generated by the polymerization reaction to be removed more efficiently. Thirdly by judicious choice of the liquid, some control over the interface tension of the liquid/pre-gel solution interface may be exercised.

This is novel and inventive in its own right and thus when viewed from a further aspect there is provided a method of fabricating a sensor probe comprising:

a. immersing the end of the fiber in a liquid forming a polymerization space;

b. applying a drop of hydrogel pre-gel solution to the end of an optical fiber; and c. exposing said pre-gel solution to an ultra-violet light source to cause polymerization therein.

Preferably the liquid comprises an organic liquid, more preferably oil. This has the properties set out above. By having a low solvent solubility, the loss of solvent from the pre-gel solution is limited. It also facilitates limiting the loss of photoinitiator if one having a low solubility in the oil or other organic liquid is selected. An oil with a low interface tension to the (normally water-based) pre-gel solution may be selected.

In accordance with preferred embodiments a photoinitiator is dissolved in the liquid. Preferably the photoinitiator is the same as that used in the pre-gel solution. The concentration of the photoinitiator is preferably greater than that in the pre-gel solution, preferably at least twice the concentration, more preferably at least three times, more preferably at least four times and most preferably five times the concentration. This has been found to give a high quality gel surface.

Where the UV light is transmitted through the liquid, the liquid should have good optical properties.

The polymerization space in which polymerization takes place in accordance with the invention could be provided by a physical chamber. However where a liquid medium is employed the Applicant has recognised that the polymerization space could instead be provided by a suitably sized droplet of the liquid medium—e.g. adhered to the end of suitable rod. This has the advantage that the volume of the polymerization space will tend to be very small and thus only a small amount of photoinitiator is required to reach the high concentration discussed earlier. Moreover it means that the liquid medium may be replaced regularly as photoinitiator is lost.

It is desirable for there to be a sharp interface between the gel droplet and the gas or liquid medium during polymerization. This aids the achievement of an optical quality surface. Where a gas medium is used this will typically result from the thin liquid-vapour interface which is determined by very short range interaction forces (of the order of one or two molecular diameters). Where a liquid medium is used it is achieved by ensuring the two liquids are immiscible.

Preferably the pre-gel solution composition and UV intensity are chosen or determined empirically such that the resulting polymer network is homogeneous—i.e. inhomogeneities such as the existence of microgels with high polymer density are on a length scale much less than the optical wavelength. This also aids the achievement of an optical quality surface.

UV light could be transmitted to the pre-gel solution by the fiber that forms part of the sensor probe itself or by free transmission through the gas or liquid in the polymerization space. In preferred embodiments though a separate, preferably large core diameter, fiber optic cable is employed for transmitting light to the sensor. This allows efficient transmission of sufficient intensity to allow rapid polymerization. It is also recognised that the rate of polymerization is also determined by: initiation, i.e. the photo-initiator concentration and type; propagation, i.e. the rate at which a monomer or polymer radical reacts with a monomer; and termination, through radical coupling, or disproportionation, when a free radical strips a hydrogen atom from an active chain.

The drop of pre-gel solution may be applied to the end of the fiber by any convenient method. In one set of embodiments the pre-gel solution is applied directly to the end by a suitable liquid delivery device, for example but not limited to one of a micro-dispenser, pipette, or ink/bubble jet head.

In a further set of preferred embodiments the drop of pre-gel solution is applied by contacting the end of the fiber on which the sensor is to be formed with a volume of the solution and withdrawing it again (of course it could instead be the fiber held static and the solution source moved). As long as they are withdrawn sufficiently slowly form each other, i.e. slowly compared to the characteristic time scale of the capillary driven motion, a "liquid bridge" is formed which elongates and eventually separates, so that a consistent volume droplet of the solution is transferred onto the end of the fiber. The actual volume is determined by the surface and interface tensions, the surface free energy, the viscosity of the solution and the diameter of the fiber end face.

The source volume could simply be provided by a reservoir; or could be in the form of a larger drop on the end of a solid or hollow rod e.g. a micro-pipette or a syringe needle. If the source of pre-gel solution is a larger drop the diameter of the rod, tube, needle etc. will also influence the final volume of the drop.

The end of the fiber which is to receive the sensor is preferably cleaved to ensure a high quality optical beam coupled from the fiber end to the sensor.

The end of the fiber is preferably treated to ensure a covalent bond between the surface of the fiber and the hydrogel sensor. For example where a glass fiber is used the end of the fiber is preferably silanized. Where a plastic fiber is used the end of the fiber is preferably provided with a surface cross-linking agent.

Fiber optic sensor probes may be fabricated one at a time in accordance with the method and apparatus of the invention. For commercial production however it is preferred to fabricate a plurality in a common polymerization space.

Where inventions defined herein comprise a plurality of steps the order in which the steps are recited is not limiting and no such inference is therefore to be drawn.

BRIEF DESCRIPTION OF THE DRAWINGS

Certain preferred embodiments of the invention will now be described, by way of example only, with reference to the accompanying drawings in which.

DETAILED DESCRIPTION OF THE PREFERRED EMBODIMENTS

Figure 1:
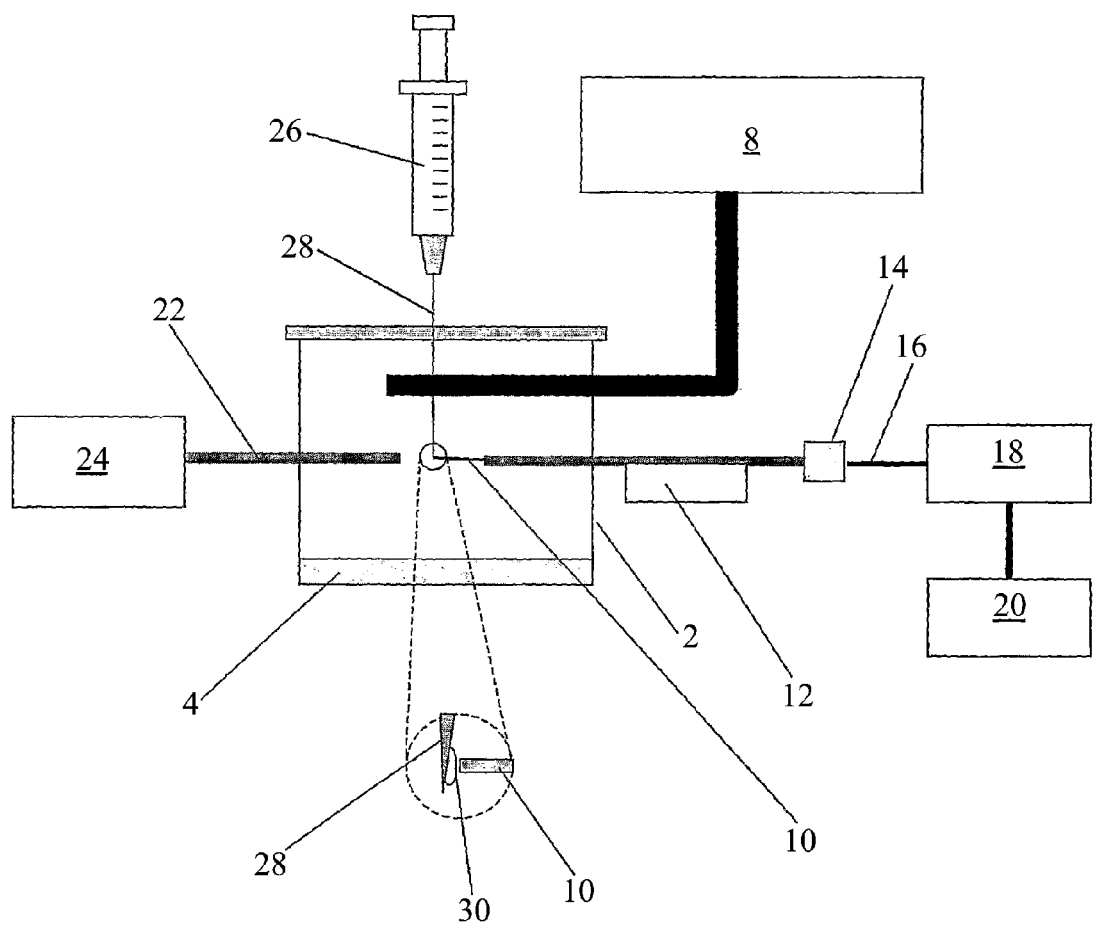
FIG. 1 is a schematic diagram showing apparatus for making a sensor probe in accordance with the invention in gas phase.

Considering FIG. 1 there may be seen apparatus for fabricating a fiber optic sensor in accordance with the invention. The apparatus is based around a polymerization chamber 2, at the bottom of which is an optional reservoir of water 4. The chamber is supplied, by means of a gas supply duct 6, with nitrogen gas from a controlled temperature and humidity source 8.

The optical fiber 10 on which the sensor is to be formed passes through a sealed aperture in the side of the chamber 2. The fiber 10 is supported on a micrometer stage 12 which permits it to be accurately advanced and retracted. A standard optical fiber coupling 14 is provided at the end of the fiber 10 and to connect it to another fiber 16 in turn coupled to an opto-electronic unit 18 containing a broadband source, a spectrometer for spectral analysis and digital signal processing for generating an interrogation optical signal and detecting the signal coming back down the fiber. The opto-electronic unit is connected to a PC 20.

A second optical fiber 22 enters the chamber 2 from the other side so as to be aligned with the first fiber 10. The second fiber 22 is a large diameter multi-mode fiber and is coupled to an ultra-violet light source 24.

A syringe 26 has a needle 28 which also passes into the chamber 2 so as to allow a drop of pre-gel solution to be applied to the end of the fiber 10.

A general description of the fabrication of a sensor probe in a gas environment will now be given followed later by a specific example. First the end of the optical fiber 10 is cleaved using a precision cleaver to give a high quality optical beam coupling to the sensor. The end of the fiber 10 is then silanized to ensure a covalent bond between the glass surface of the fiber end and the hydrogel sensor. If a plastic fiber is used a cross-linking agent may be applied instead. For example plastic optic fibers are commonly made from polymethylmethacrylate (PMMA). A PMMA fiber can be prepared for cross-linking by oxidizing the surface by ultraviolet/ozone exposure. The activated PMMA surface is then reacted with 3-methacryloxypropyltrimethoxysilane, a cross-linking agent, forming pendant methacrylate groups that can act as polymerization anchor points for acrylamide monomers during the UV polymerization.

The fiber 10 is then inserted into the chamber 2 using the micrometer stage 12 to control precisely the separation between the fiber 10 and the multimode fiber 22 coupled to the UV light source 24.

A droplet of hydrogel pre-gel solution containing the hydrogel monomer is then put onto the end of the fiber 10. This is done by firstly depressing the plunger of the syringe 26 in order to express a droplet of solution 30 using the syringe

26. This may be seen in the detail enlargement of FIG. 1. The tip of the fiber 10 is then advanced towards the droplet 30 until it contacts it. The fiber 10 is then retracted thereby forming a liquid bridge between the needle 28 and the tip of the fiber 10. Eventually this separates leaving a drop of hydrogel pre-gel solution on the end of the fiber 10. The size and shape of the hydrogel is determined by the source droplet's volume, the surface tension, interface tension and surface free energy.

The UV source is then energized so as to expose the droplet at the end of the fiber 10 to UV light. This causes rapid polymerization which ensures an optical quality finish and a high degree of homogeneity of the hydrogel. During the polymerization process the end surface quality, droplet volume and volume rate of change are monitored by the opto-electronic unit 18 using a spectrometer to analyse the interference signal generated by passing a near-infra-red signal down the fiber 10. These are used to control one or more parameters of the process such as the timing of the UV exposure, the humidity in the chamber (controlled by adjusting the proportion of dry nitrogen), gas flow rate and the temperature of the chamber. The gas flow rate and humidity control the evaporation of solvent from the monomer solution.

After polymerization is complete the fiber probe 10 is placed in a stabilizing buffer solution. Thereafter it may be stored in buffer solution or rapidly dehydrated in a dry atmosphere or ethanol; and stored in a dry atmosphere.

Although the fabrication of only one sensor is described, many may be produced in parallel. In these circumstances it may only necessary to interferometrically monitor the quality of one fiber in each chamber. Furthermore when fabrication is achieved of a hydrogel sensor having an optical quality dome-shaped surface, exhibiting a high degree of homogeneity, covalently bound to the end of the fiber and porous; the process parameters used to achieve it can be reproduced repeatedly in order to fabricate further sensors in the same or a similar chamber. Thus the initial production carried out using monitoring can in some senses be seen as setting up or calibrating the process. Thereafter fabrication can be carried out in the chamber in accordance with the invention under controlled conditions of temperature, humidity, gas flow rate etc. Corresponding sensors forming part of respective feedback control systems are employed in order to effect the aforementioned control.

Figure 2:
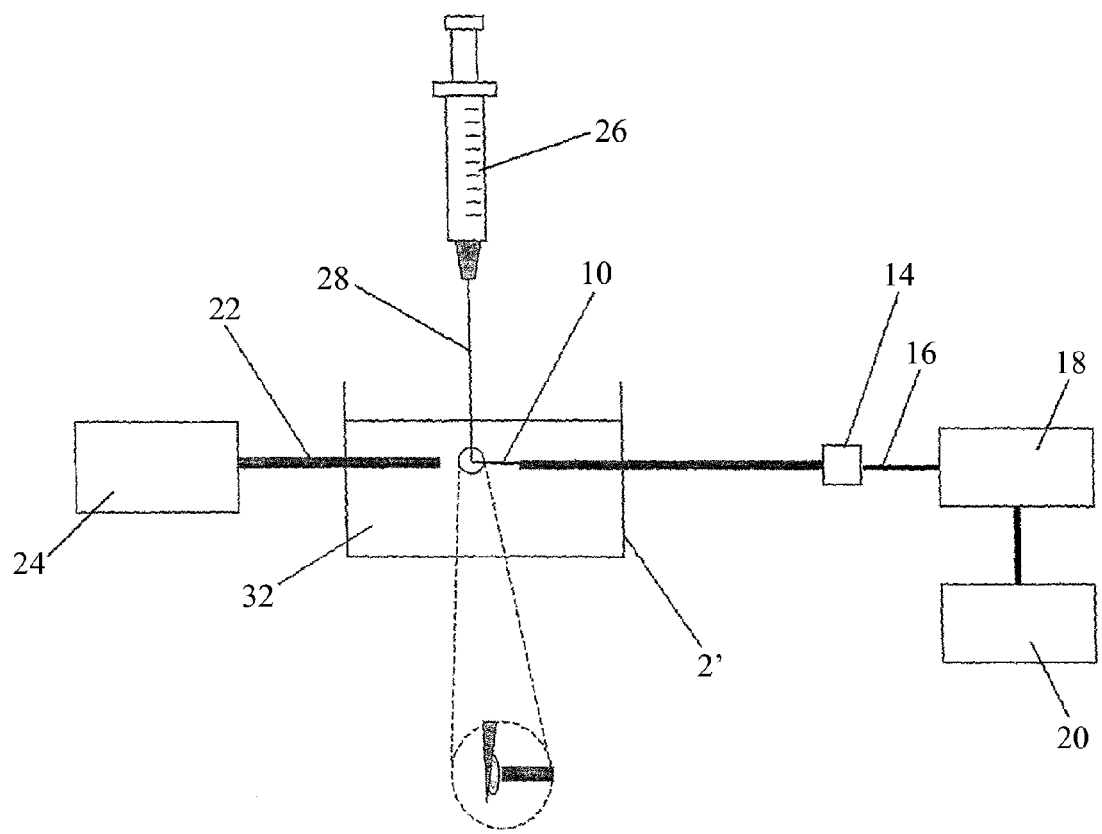
FIG. 2 is a schematic diagram showing apparatus for making the sensor in a liquid phase.

FIG. 2 shows schematically a second embodiment of the invention where the polymerization is carried out in oil. This embodiment is very similar to the first except of course that the chamber 2' contains oil 32 in this case. The fiber 10 on which the sensor is formed enters the chamber 2' from one side as in the first embodiment. Either the fiber 10 or the UV fiber 22 is mounted so as to horizontally translatable.

The procedure followed is similar to that for the gas phase procedure and thus only the differences are described. Again a specific example follows later. In the liquid phase procedure solvent and photoinitiator loss is controlled by using oil 32 as the liquid in which the fiber 10 is immersed since the solvent and photoinitiator have very low solubilities in the oil. Photoinitiator is also dissolved in the oil, e.g. to a concentration of five times that of the pre-gel solution, to give further control of photoinitiator loss and a high quality optical gel surface. The oil has good optical qualities and so does not excessively scatter the UV light which is incident from above. The pre-gel solution is added to the end of the fiber from a syringe 26 which is used to express a blob of solution 30 that is then contacted with the end of the fiber.

EXAMPLE 1

Hydrogel Formation in Gas Phase Environment

Acryl silanization of a clean and dry optical fiber end (fiber diameter 125 microns) was done by first incubating the fiber in 1 Molar (M) of NaOH for 20 minutes followed by washing in water and drying. In the next step the fiber was incubated in 0.01 M HCl for 20 minutes followed by washing in water. The silanization step was performed in a mixture of water (4.9 ml) having a pH of 3.5 (adjusted with 0.1 M HCl) and [γ-(methacryloxy)-propyl] trimethoxysilane (100 μl) for 1 hour at room temperature. The water [γ-(methacryloxy)-propyl] trimethoxysilane mixture was stirred vigorously for 15 minutes prior to use. After silanization the fiber was washed with water and dried.

Although an NaOH incubation step is carried out if the fiber has been handled or otherwise contaminated, it can be avoided by cutting the fiber just before silanization.

A stock solution of 30% acrylamide (AAm) and 2 mol % N,N'-methylenebisacrylamide (Bis) was made by mixing 3.00 g AAm and 0.1328 g Bis in 0.02 M phosphate buffer pH 7.4 to a total volume of 10 ml. The photoinitiator solution, 100 mM 1-hydroxycyclohexyl phenyl keton, was made by dissolving 0.0102 g 1-hydroxycyclohexyl phenyl ketone in 500 μl ethyleneglycol. The stock and photoinitiator solution were stored cold (4° C.) and dark for maximum three months and two weeks, respectively.

From the stock and the photoinitiator solutions a 10% gel solution, containing 98 mol % AAm, 2 mol % Bis and 0.125 mol % photoinitiator was mixed and stored dark.

The polymerization of the hydrogel sensor head was done inside a Plexiglas chamber containing a moistened $N_2$ atmosphere. The bottom of the chamber was filled with distilled water. In addition, the chamber humidity was adjusted by varying the portion of dry to moistened $N_2$ gas flowing into the chamber so the size of a droplet of gel solution was held constant (no swelling or shrinking). The light guide from the UV lamp, a 400 micron multimode optical fiber, entered the chamber horizontally, and from the opposite direction a silanized optical fiber (diameter 125 microns) for the sensor head was centered end-to-end towards the multimode fiber. The distance between these two fibers was set to 500 micron.

Figure 3A:
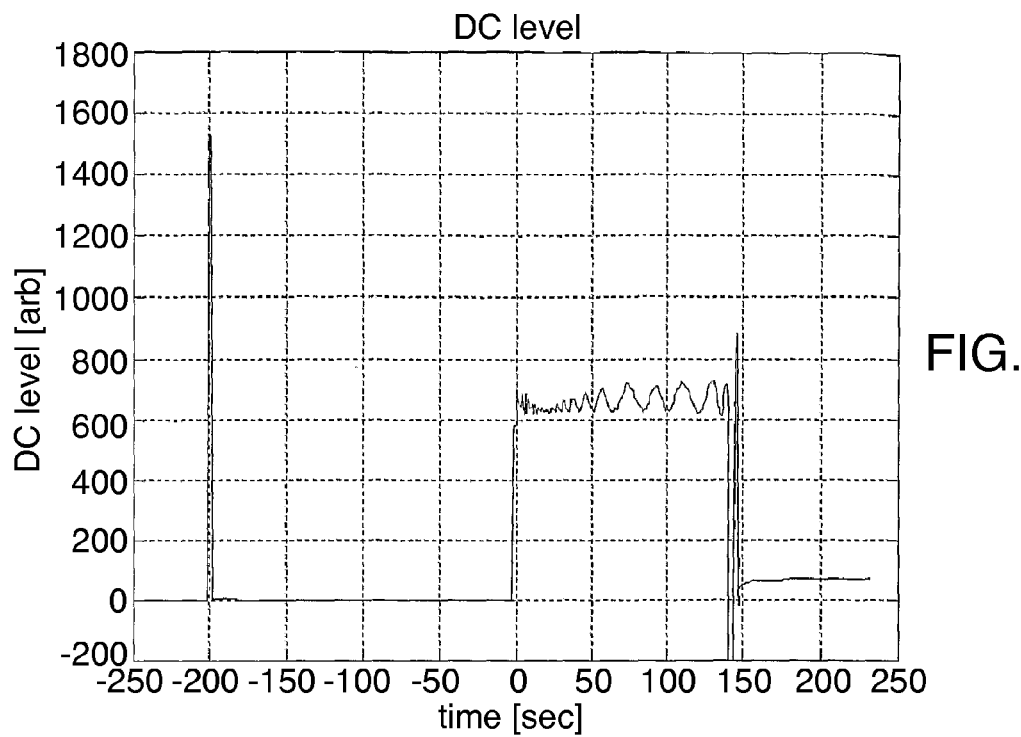
FIGS. 3a to 3d show plots of various parameters against time achieved in an example method.
Figure 3B:
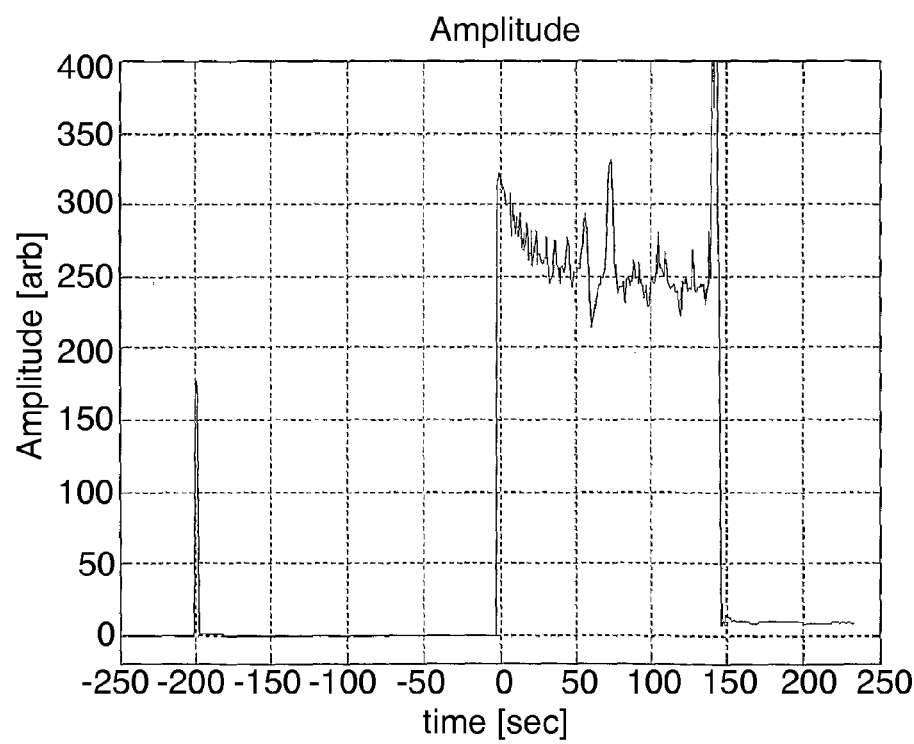
Figure 3C:
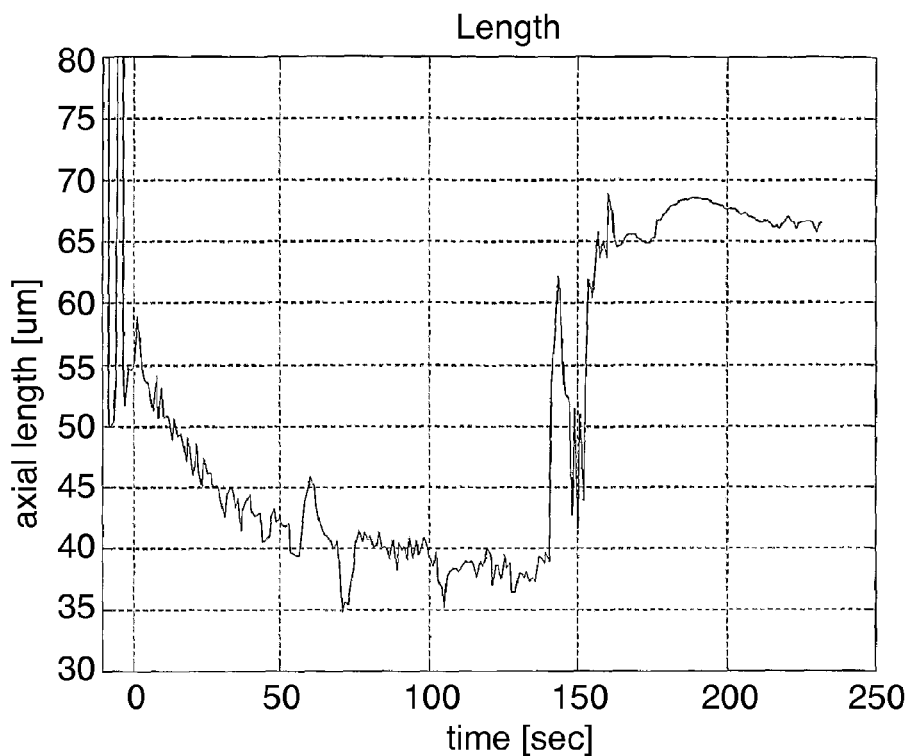

With a pipette (20 μl) and a syringe needle (25G), gel solution was deposited on the end of the optical fiber forming a dome-shaped droplet. UV radiation (Medicure MC 4000 lamp) was used for polymerization. Exposure time was 130 seconds. The UV flux was set by measuring the relative UV power of an approx. 1 $W/cm^2$ high pressure mercury lamp coupled to the optical fiber, using an optical detector at the proximal end of the optical (sensor) fiber. The axial length of the droplet/hemisphere (in μm), the axial length change (in μm) and the amplitude of the signal reflected from the surface of the hemisphere, were all recorded during the polymerization step. These are shown in FIGS. 3a to 3c.

Immediately after the UV exposure was ended, the optical fiber with sensor head at the end was placed in a physiological phosphate buffer with 0.138 M NaCl and pH 7.40.

EXAMPLE 2

Hydrogel Formation in Liquid Phase Environment

Acryl silanization of a clean and dry optical fiber end (fiber diameter 125 microns) was done by first incubating the fiber in 1 M NaOH for 20 minutes followed by washing in water and drying. In the next step the fiber was incubated in 0.01 M HCl for 20 minutes followed by washing in water. The silanization step was performed in a mixture of water (4.9 ml) having a pH of 3.5 (adjusted with 0.1 M HCl) and [γ-(methacryloxy)-propyl] trimethoxysilane (100 µl) for 1 hour at room temperature. The water [γ-(methacryloxy)-propyl] trimethoxysilane mixture was stirred vigorously for 15 minutes prior to use. After silanization the fiber was washed with water and dried.

Again the NaOH incubation step may not be required.

A stock solution containing 30% acryl amide (AAm) and 2 mol-% N,N'-methylenebis-acrylamide (Bis) was prepared by mixing 3.00 g AAm and 0.1328 g Bis in 0.02 M phosphate buffer pH 7.4 to a total volume of 10 ml. In 500 ml ethylene glycol 0.0102 g hydroxycyclo-hexyl phenyl ketone (photo initiator), was dissolved giving a 100 mM solution. The stock and photo initiator solutions were stored in the dark at low temperature (4° C.) for maximum three months and two weeks respectively.

The polymerization of the hydrogel sensor head was done in a small beaker filled with hexadecane (oil). In particular the oil used was Squalane, product number 234311 from the Aldrich Chemical Company, Inc. The oil had the same photoinitiator used to prepare the pre-gel solution dissolved in it. The concentration of photoinitiator in the oil was five times that in the pre-gel solution. This was found to prevent loss of photoinitiator into the oil and allowed the production of a high quality gel surface. The Applicant has found that the photoinitiator in the oil helps in defining a high quality gel surface.

The light guide from the UV lamp, a 400-micron multimode fiber, was directed horizontally, and from the opposite direction the acryl silanized optical fiber for receiving the sensor head was centered end-to-end towards the multimode fiber. The distance between these two fibers was set to 500 micron.

From the stock and the photo initiator solutions a 20% gel solution was prepared, containing 98 mol-% Aam, 2 mol-% Bis and 0.125 mol-% photo initiator.

With a 2.5 µl pipette gel solution was deposited on the end of the optical fiber immersed in Squalane forming a dome-shaped droplet. UV radiation (Medicure MC 4000 lamp) was used for polymerization. Exposure time was 90 seconds. The axial length of the droplet/hemisphere (in µm), the axial length change (in nm) and the amplitude of the signal reflected from the surface of the hemisphere, were all recorded during the polymerization step.

After the UV exposure was ended, the optical fiber FP sensor head was placed in physiological phosphate buffer with 0.138 M NaCl and pH 7.40.

Results

As previously described, the hydrogel probe preparation process is monitored by analyzing the interferometric signal from the Fabry-Perot hydrogel sensor by coupling a near-infrared source and a spectrometer to the optical fiber.

Figure 3D:
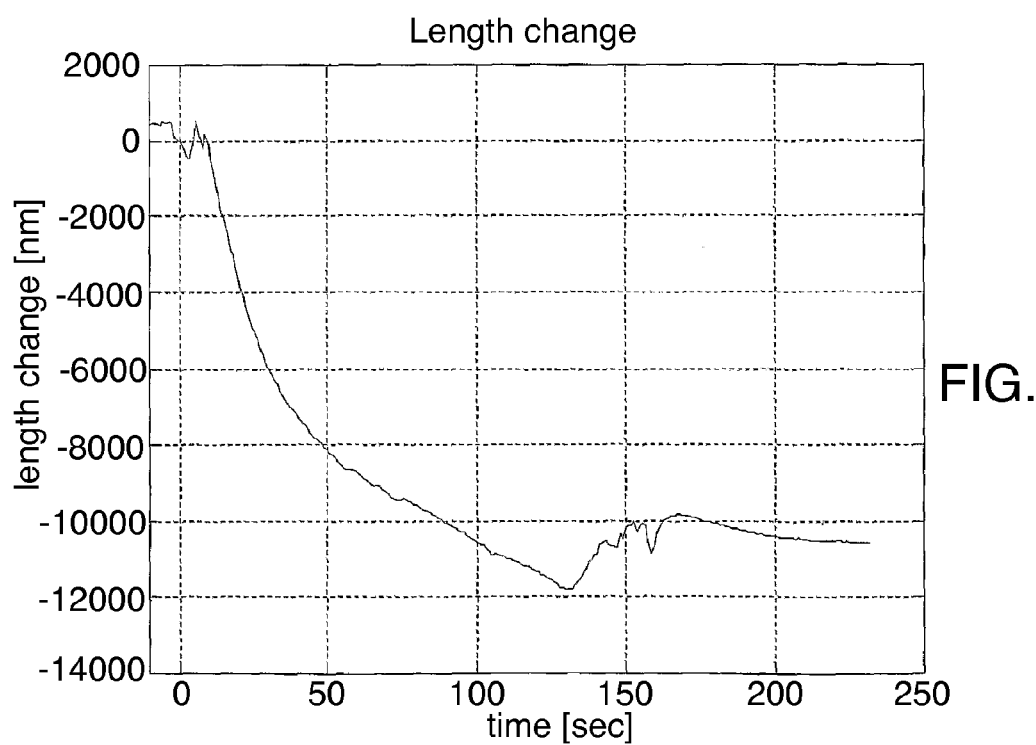

The following parameters were logged for preparation of a 10% polyacrylamide gel with 2 mol % crosslinker: the amplitude of the reflected signal, plotted in FIG. 3b, which is a measure of the hydrogel surface quality, curvature, and symmetry of the dome; the DC component of the reflected signal plotted in FIG. 3a which is a measure of the fiber end quality or the polymer fraction in the hydrogel; the axial length of the hydrogel droplet dome, plotted in FIG. 3c; and the axial length change of the hydrogel droplet dome, plotted in FIG. 3d.

Interferometric monitoring of the hydrogel preparation process was carried out in the following stages listed below. a) Before the monomer solution is placed at the fiber end a DC signal of 1500 (at time −200 sec) was measured as may be seen in FIG. 3a. This demonstrates a high optical quality fiber cut. b) Prior to polymerization the chamber conditions were adjusted to result in a stable droplet volume and high quality hydrogel. The chamber conditions are set to give an initial length change during polymerization (after the UV light is turned on) of around −4 µm/10 sec (FIGS. 3 c and d, time interval from 0-20 sec), and a length change of around +1 µm/10 sec after the polymerization is completed and the UV light is turned off (time interval from 130-150 sec). These conditions are set during one or more test runs prior to the polymerization runs shown here. c) At time −2 seconds, after the droplet is positioned at the fiber end, an amplitude of 320 was measured (FIG. 3b) which confirms that a symmetric droplet is positioned at the fiber end. d) At the same time the length of the droplet was measured as 55 µm (FIG. 3c). e) During the UV exposure, starting at time 0 sec, the droplet shrinks due to heat generation from the polymerization reaction. (FIGS. 3 c and d). f) After the polymerization reaction is complete at 130 seconds, the rate of shrinkage is decreased (FIGS. 3 c and d) demonstrating the equilibrium in the chamber under UV exposure, i.e. a high water vapor pressure to control evaporation. This chamber condition is set at the start of the procedure (point (b) above). g) After the UV exposure is turned off at time 130 sec, the hydrogel volume increases to reach a new equilibrium (FIGS. 3 c and d). h) The amplitude after polymerization is maintained high at 245 (FIG. 3b), i.e. the hydrogel dome-shape is symmetric with respect to the axis of the optical fiber axis and the hydrogel is homogeneous. i) At time 146 seconds the fiber with the hydrogel dome sensor at the end is placed in a buffer solution as seen by the instantaneous drop in DC and amplitude. (FIGS. 3a and 3b). j) After about one minute the hydrogel volume is in a stable equilibrium with the buffer, with a length of 66 µm, DC level of 68, and amplitude of 9. (FIGS. 3a, 3b and 3c). (This parameter set corresponds to a high quality hydrogel Fabry-Perot interferometer probe.)

Figure 4:
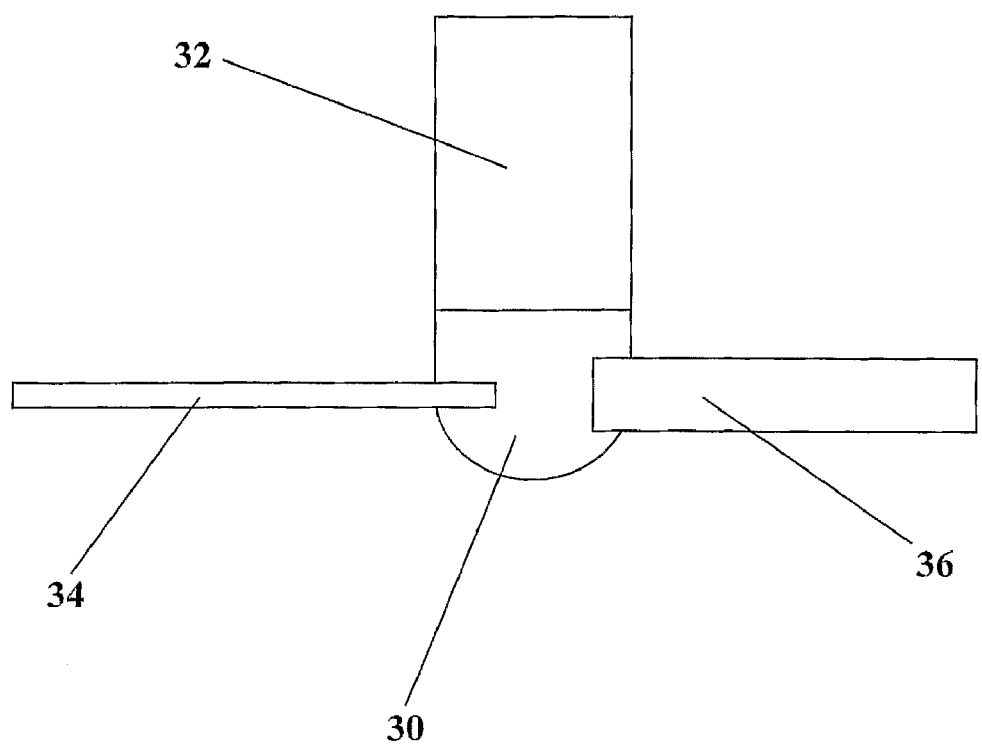
FIG. 4 is a schematic diagram showing an alternative method of making the sensor in a liquid phase.

A further embodiment is shown in FIG. 4. In this embodiment the polymerization reaction also takes place in oil. However rather than being received in a container forming the polymerization space, the oil is in the form of a droplet of oil 30 immobilised at the end of a rod 32. The fiber 34 forming the sensor probe and the fiber 36 supplying the UV radiation which promotes polymerization are inserted into opposite sides of the droplet. The polymerization reaction may therefore take place as described in relation to the second embodiment. However in this embodiment the very low volume of the oil droplet 30 means that only a small absolute amount of photoinitiator need be provided in the droplet 30 to give a sufficient concentration to prevent excess loss of photoinitiator from the pre-gel material. The oil 30 can therefore be replaced regularly to ensure that sufficient concentration of photoinitiator is maintained.

In one example the rod 32 used is 4 mm in diameter giving an oil droplet of 25 microliters; the sensor fiber 34 is 125 microns in diameter; and the UV irradiation fiber 36 is 400 microns in diameter.

While the present invention has been illustrated and described with respect to a particular embodiment thereof, it should be appreciated by those of ordinary skill in the art that various modifications to this invention may be made without departing from the spirit and scope of the present invention.

What is claimed is:

1. A method of fabricating a sensor probe comprising:
   placing the end of an optical fiber in a polymerization space;
   applying a drop of hydrogel pre-gel solution to the end of the fiber;
   exposing said pre-gel solution to an ultra-violet light source to cause polymerization therein; and
   monitoring a light signal that has passed down said optical fiber in order to monitor said polymerization.

2. The method as claimed in claim 1 comprising monitoring one or more parameters of said light signal from the group comprising: the average level of the signal, the variation of amplitude with wavelength, the period of the signal and the phase of the signal.

3. The method as claimed in claim 1 comprising using said monitoring of the polymerization process for active control of one or more parameters controlling the polymerization process.

4. The method as claimed in claim 3 comprising using automatic feedback control.

5. The method as claimed in claim 1 comprising:
   storing one or more of the polymerization process parameters; and
   using said parameter(s) to control a subsequent fabrication of a sensor probe without monitoring.

6. A method of fabricating a plurality of sensor probes comprising:
   placing the end of a further optical fiber in a polymerization space;
   applying a drop of said hydrogel pre-gel solution to the end of the further fiber; and
   exposing said pre-gel solution to an ultra-violet light source to cause polymerization therein wherein at least one of the temperature of the space, the exposure time of the ultra-violet light, the intensity of the ultra-violet light or the flux of the ultra-violet light is controlled according to a criterion predetermined from monitoring of a light signal that passed down an optical fiber during a previous fabrication of a sensor probe carried out as claimed in claim 1.

7. The method as claimed in claim 1 comprising carrying out said polymerization in a gas.

8. The method as claimed in claim 7 comprising passing a continuous gas flow over the end of the fiber.

9. The method as claimed in claim 7 wherein the gas is substantially free of oxygen.

10. The method as claimed in claim 7, wherein said gas comprises humidified nitrogen.

11. The method as claimed in claim 7 comprising controlling the flow velocity and/or humidity of the gas in order to control evaporation of solvent from the monomer solution.

12. The method as claimed in claim 7 comprising controlling one or more parameters selected from the group comprising: ultra-violet exposure time, intensity or flux; humidity; gas flow; and temperature.

13. The method as claimed in claim 12 comprising controlling said parameter(s) to counter the heat generated by the polymerization reaction.

14. The method as claimed in claim 13 comprising controlling at least one of temperature, humidity and gas velocity.

15. The method as claimed in claim 7 comprising maintaining a partial pressure of water in the polymerization space at or near saturation pressure.

16. The method as claimed in claim 1 comprising carrying out said polymerization in a liquid.

17. The method as claimed in claim 1 wherein the pre-gel solution composition and UV intensity are such that the resulting hydrogel polymer network is homogeneous.

18. The method as claimed in claim 1 comprising transmitting said UV light to the pre-gel solution using a second fiber optic cable.

19. The method as claimed in claim 1 comprising initially cleaving the end of the fiber.

20. The method as claimed in claim 1 comprising applying said pre-gel solution to the end of the fiber by contacting the end of the fiber is to be formed with a volume of said pre-gel solution and withdrawing said fiber and said volume of solution relative to each other.

21. The method as claimed in claim 1 comprising treating the end surface of the fiber to ensure a covalent bond between the surface of the fiber and the hydrogel sensor.

22. A sensor probe made according to a method as claimed in claim 1.

23. A method of fabricating a sensor probe comprising:
    immersing the end of an optical fiber in a liquid forming a polymerization space;
    applying a drop of hydrogel pre-gel solution to the end of the optical fiber; and
    exposing said pre-gel solution to an ultra-violet light source to cause polymerization therein.

24. The method as claimed in claim 23 wherein said liquid is an organic liquid.

25. The method as claimed in claim 23 wherein said liquid comprises oil.

26. The method as claimed in claim 23 wherein said polymerization space comprises a droplet of liquid.

27. An apparatus for fabricating a sensor probe comprising:
    an optical fiber having a drop of hydrogel pre-gel solution on one end thereof;
    a polymerization space receiving said fiber end;
    an ultra-violet light source arranged to expose said pre-gel solution to said light to cause polymerization therein; and
    a monitoring arrangement for monitoring a light signal that has passed down said optical fiber in order to monitor said polymerization.

28. The apparatus as claimed in claim 27 comprising a monitoring arrangement for monitoring one or more parameters of said light signal from the group comprising: the average level of the signal, the variation of amplitude with wavelength, the period of the of the signal and the phase of the signal.

29. The apparatus as claimed in claim 27 comprising an active control arrangement for actively controlling one or more parameters of said polymerization process using said monitoring.

30. The apparatus as claimed in claim 29 wherein said active control arrangement is arranged to control said parameter(s) using automatic feedback.

31. The apparatus as claimed in claim 27 comprising a storage arrangement for storing one or more of the polymerization process parameters.

32. The apparatus as claimed in claim 31 arranged to fabricate a subsequent probe using polymerization parameter(s) stored in said storage arrangement.

33. The apparatus as claimed in claim 27 wherein said fiber is immersed in a gas.

34. The apparatus as claimed in claim 33 comprising a gas supply arrangement for passing a continuous gas flow over the end of the fiber.

35. The apparatus as claimed in claim 33 comprising a source of gas substantially free of oxygen.

36. The apparatus as claimed in claim 35 wherein said gas comprises humidified nitrogen.

37. The apparatus as claimed in claim 33 comprising a control arrangement for controlling the flow velocity and/or humidity of the gas in order to control evaporation of solvent from the monomer solution.

38. The apparatus as claimed in claim 33 comprising a control arrangement for controlling one or more parameters selected from the group comprising: ultra-violet exposure time, intensity or flux; humidity; gas flow; and temperature.

39. The apparatus as claimed in claim 38 wherein said a control arrangement for controlling said parameter(s) is arranged to counter the heat generated by the polymerization reaction.

40. The apparatus as claimed in claim 39 comprising a control arrangement for controlling at least one of temperature, humidity and gas velocity.

41. The apparatus as claimed in claim 33 comprising an arrangement to maintain a partial pressure of water in the polymerization space at or near saturation pressure.

42. The apparatus as claimed in claim 27 wherein the end of said fiber is immersed in a liquid.

43. The apparatus as claimed in claim 27 wherein the pre-gel solution composition and UV intensity are such that the resulting hydrogel polymer network is homogeneous.

44. The apparatus as claimed in claim 27 comprising a second fiber optic cable for transmitting UV light to the end of the first fiber.

45. The apparatus as claimed in claim 27 wherein the end surface of the fiber is treated to ensure a covalent bond between the surface of the fiber and the hydrogel sensor.

46. An apparatus for fabricating a sensor probe comprising:
a polymerization space containing a liquid;
an optical fiber having a drop of hydrogel pre-gel solution on one end thereof, said end being immersed in said liquid;
an ultra-violet light source arranged to expose said pre-gel solution to light from said ultra-violet light source to cause polymerization therein.

47. The apparatus as claimed in claim 46 wherein said liquid is an organic liquid.

48. The apparatus as claimed in claim 46 wherein said liquid comprises oil.

49. The apparatus as claimed in claim 46 wherein said polymerization space is formed by a droplet of said liquid.

* * * * *